United States Patent [19]

Rutzen et al.

[11] Patent Number: 4,825,004

[45] Date of Patent: Apr. 25, 1989

[54] PROCESS FOR THE PRODUCTION OF ALKANE POLYOLS

[75] Inventors: Horst Rutzen, Langenfeld; Gerhard Stoll, Waldkirch, both of Fed. Rep. of Germany

[73] Assignee: Henkel Kommanditgesellschaft auf Aktien, Duesseldorf, Fed. Rep. of Germany

[21] Appl. No.: 205,987

[22] Filed: Jun. 13, 1988

[30] Foreign Application Priority Data

Jun. 13, 1987 [DE] Fed. Rep. of Germany ....... 3719790

[51] Int. Cl.$^4$ ..................... C07C 29/136; C07C 31/22
[52] U.S. Cl. ...................................... 568/864; 568/860
[58] Field of Search ................................ 568/864, 860

[56] References Cited

U.S. PATENT DOCUMENTS

| | | | |
|---|---|---|---|
| 2,492,201 | 12/1949 | Swern et al. | 568/860 |
| 3,169,139 | 2/1965 | D'Addieco | 568/860 |
| 4,172,961 | 10/1979 | Henery et al. | 568/864 |
| 4,410,744 | 10/1983 | Campbell et al. | 568/864 |
| 4,584,419 | 4/1986 | Sharif et al. | 568/864 |
| 4,652,685 | 3/1987 | Canse et al. | 568/864 |

FOREIGN PATENT DOCUMENTS 3033441  4/1982  Fed. Rep. of Germany ...... 568/864

OTHER PUBLICATIONS

B. Palameta, M. Prostenik, Tetrahedron 19 (10) (1963) 1463.
F. J. Julietti et al, Soc. 1960 (11) 4514.
R. Subbarao, K. T. Achaga, J. Sci Ind. Res. (India) 19B (1960) 482–484.
F. J. Julietti et al., Chem. Ind. 27 (1060) 874.

Primary Examiner—J. E. Evans
Attorney, Agent, or Firm—Ernest G. Szoke; Wayne C. Jaeschke

[57] ABSTRACT

A process for the production of alkane polyols and especially alkane triols where mono- and/or poly-epoxidized fatty acids and/or fatty acid esters and mixtures thereof, especially derivates of natural fatty acids, are reacted with short-chain alkane-carboxylic acids such as formic or acetic acids; and the ester alcohols produced are hydrogenated on a hydrogenation catalyst such as those containing copper chromite at elevated temperature and pressure. The maximum possible number of alcohols groups per molecule can be formed in this way thus producing alkane triols, for example, which are useful in cosmetic formulations as well as in polyurethanes.

18 Claims, No Drawings

PROCESS FOR THE PRODUCTION OF ALKANE POLYOLS

BACKGROUND OF THE INVENTION

1. Field of the Invention

This invention relates to a process for the production of alkane polyols from epoxidized fatty acids and/or fatty acid esters.

2. Statement of Related Art

Long-chain polyols are produced from natural unsaturated fatty acids or esters thereof which are converted with potassium permanganate, percarboxylic acid or other suitable reagents into the polyhydroxy fatty acids or esters thereof. This is followed by reduction with lithium alanate or sodium to the polyol (B. Palameta, M. Prostenik, Tetrahedron 19 (10) (1963) 1463; F. J. Julietti et al., Soc. 1960 (11) 4514).

When percarboxylic acids are used to hydroxylate the double bonds, epoxides are initially formed. The epoxides are converted into the corresponding ester alcohols in the presence of carboxylic acids with ring opening. According to the prior art, the ester alcohols are hydrolyzed to the polyhydroxy-carboxylic acids and reduced with lithium alanate. The reduction is preferably preceded by esterification with a short-chain alcohol.

When the reaction is carried out with ricinoleic acid as starting material, a tetrol is obtained as the end product (R. Subbarao, K. T. Achaya, J. Sci. Ind. Res. (India) 19B (1960) 482–84).

Epoxy fatty acids also have been reduced directly to diols with lithium alanate (F. J. Julietti et al., Chem. Ind. 27 (1960) 874). However, a potential alcohol group is lost in this reaction.

Unfortunately, the prior processes do not provide an efficient and economical way of providing high quality alkane polyol products having a maximum number of alcohol groups. Therefore, an object of the present invention is to provide a process for the production of alkanetriols and alkane polyols from mono- and/or poly-epoxidized fatty acids and/or fatty acid esters, in which the maximum number of possible alcohol groups per molecule is formed; and in which hydrolysis steps are unnecessary.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that alkane polyols can be obtained particularly efficiently and economically from commercially available epoxidized unsaturated fatty acid esters. Epoxidized fatty acids, esters or mixtures thereof are first treated with a short-chain alkane carboxylic acid such as, e.g., formic acid or acetic acid for several hours at elevated temperature, preferably in the presence of a catalyst such as, e.g., an alkali metal (preferably sodium or potassium) formate or acetate. Ring opening to the ester alcohol occurs, for example, as depicted in accordance with the following equation:

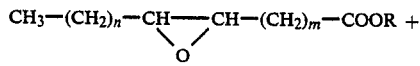
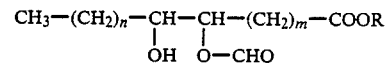

Where n and m are integers from 0 to 20 and R is H or mono-, di-, and tri-alcohol radicals containing 1-8 carbon atoms.

The ester alcohol is then catalytically hydrogenated in a single step such that both ester groups are simultaneously converted into alcohol groups depicted in accordance with the following equation:

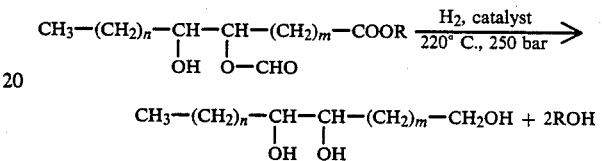

The present invention relates to a process for the production of alkane polyols and especially alkanetriols which comprises reacting mono- and/or poly-epoxidized fatty acids and/or fatty acid esters or mixtures thereof with short-chain alkane carboxylic acids under epoxide ring opening conditions to produce ester alcohols of the epoxidized fatty acids or esters. Epoxide ring opening conditions are known in the prior art and include refluxing a suitable epoxidized fatty acid or ester with a short-chain alkane carboxylic acid at a temperature preferably between 125° C. and 200° C. for 2 to 6 hours at atmospheric pressure. The ester alcohols are then passed through a catalytic hydrogenation zone maintained under conditions to convert the ester alcohols to alkane polyols which are thereafter recovered as product.

The epoxidized fatty acids and/or fatty acid esters required for the process according to the invention are prepared by known methods, for example, from the reaction of mono- and/or polyunsaturated fatty acids and/or fatty acid esters and peroxy acetic acid.

The process of the present invention enables production of polyol products which contain the maximum number of possible alcohol groups per molecule. Accordingly, the polyols produced by the process of the invention are especially well suited for use as consistency generators for cosmetic preparations and as the polyol component for the production of polyurethanes.

In one embodiment of the process of this invention, epoxidized fatty acids and/or fatty acid esters are employed which have a chain length of 4 to 24 carbon atoms in the fatty acid component. At the same time, the alcohol components of the fatty acid esters contain mono-, di- and tri-alcohol radicals containing 1 to 8 carbon atoms. It is, of course, possible to subject not only individual fatty acids and/or fatty acid esters to the process according to the invention, but also mixtures of epoxidized fatty acids and/or mixtures of epoxidized fatty acid esters and mixtures of epoxidized fatty acids and fatty acid esters.

In general, the epoxidation products of natural or synthetic unsaturated fatty acid esters are useful in the process of this invention. In a preferred embodiment, suitable starting materials include the epoxidation products of natural oleic acid esters, soybean oil fatty acid esters, erucic acid esters, rapeseed oil fatty acid esters, linseed oil fatty acid esters, safflower oil fatty acid esters and cottonseed oil fatty acid esters or beef tallow.

Epoxidized fatty acid esters of which the alcohol component is derived from ethanol and/or glycerol are particularly preferred for the purposes of this invention.

Natural unsaturated fatty acids and/or fatty acid esters which are obtained from technical beef tallow generally contain a double bond. Accordingly, in one preferred embodiment of the process according to this invention, such double bond is epoxidized yielding mono-epoxidized fatty acids and/or fatty acid esters and mixtures thereof. Accordingly, it is particularly preferred in accordance with the invention to use epoxidized technical oleic acid methyl ester, for example, having the following chain length distribution (% by weight):

| | |
|---|---|
| 0 to 2% $C_{12}$ | |
| 2 to 5% $C_{14}$ | |
| 5 to 7% $C_{16}$ | |
| 5 to 7% $C_{16}$ | mono-unsaturated |
| 1 to 3% $C_{18}$ | |
| 70 to 75% $C_{18}$ | mono-unsaturated |
| 8 to 12% $C_{18}$ | di-unsaturated |
| 0 to 1% $C_{18}$ | tri-unsaturated |
| and 0 to 4% higher | | with the epoxide value of 4.6% by weight epoxide oxygen.

The epoxidized fatty acids and/or fatty acid esters are reacted with alkanecarboxylic acids and/or alkali metal salts thereof to produce the corresponding ester alcohols. The shortchain alkane carboxylic acids are preferably $C_1$–$C_8$ and most preferably $C_1$–$C_3$. In this regard, it is preferred to select the short-chain alcohol with which the epoxide fatty acid is esterified and the carboxylic acid with which the epoxide ring was opened in such a way that a uniform, short-chain alcohol is obtained after the hydrogenation reaction. In one embodiment of the invention, therefore, the chemical constitution of the alkyl radicals of the alkanecarboxylic acids and of the alcohol component of the epoxidized fatty acid esters is the same. For example, epoxidized fatty acid methyl esters are advantageously reacted with formic acid in order to produce a methanol moiety during the hydrogenation reaction. Other preferred alkanecarboxylic acids according to the invention are acetic acid and/or propionic acid and, optionally, mixtures thereof and/or sodium and/or potassium salts thereof. However, it is preferred in accordance with the invention to select a carboxylic acid in such a way that a uniform short-chain alcohol is obtained after the hydrogenation reaction. Accordingly, combinations of methyl esters and formic acid, ethyl esters and acetic acid and n-propyl esters and propionic acid are advantageous for the purposes of the invention.

When methyl esters are combined with acetic acid, a methanol/ethanol mixture is formed and which requires separation by distillation in the absence of a specific potential application for the mixture.

The ester alcohol formed by the reaction with an alkanecarboxylic acid is then hydrogenated over a suitable hydrogenation catalyst, for example, over a copper chromite catalyst under conditions including an elevated temperature and pressure. In one preferred embodiment of the invention, a particulate copper-and/or zinc-containing catalyst is used at temperature of 150° to 300° C. and at pressures of 200 to 300 bar. An oxidic feed-bed catalyst is preferably employed and the hydrogenation reaction is carried out with an excess of hydrogen of 50 to 500 times the theoretically necessary quantity. The hydrogenation gas is preferably circulated at a rate of 1 to 4 pressure liter per hour and per liter of catalyst volume. A solvent is employed optionally and suitable solvents are, for example, aliphatic $C_1$–$C_4$ alcohols, particularly those alcohols which are also formed during the catalytic hydrogenation. The preparation of a barium-containing copper chromite catalyst from barium nitrate, for example, copper nitrate and ammonium dichromate is described in German Patent Publication No. 17 68 313 B2 which also describes the production of a copper-zinc catalyst from zinc sulfate heptahydrate and copper sulfate pentahydrate. Copper- and/or zinc-containing catalysts of the type used for the hydrogenation of fatty acids to fatty alcohols are useful as catalysts in the process of this invention. Accordingly, in addition to copper and/or zinc, the hydrogenation catalysts may contain other metals, such as, for example, aluminum, chromium, vanadium, tungsten, molybdenum and, in particular, activating additives, such as barium and cadmium.

The catalysts can be used in compact form, for example in tablet form, or on suitable supports, for example, pumice, silica gel, alumina, as well as natural and synthetic zeolites.

EXAMPLES

Example 1

A. Preparation of the ester alcohol 324.5 g (1.0 mol) epoxystearic acid methyl ester (epoxide value 4.93%, molecular weight M calculated therefrom 324.5) and 50.6 g (1.1 mol) formic acid were stirred for 3 hours at 150° C. and a gentle reflux was established. After the reaction, a clear, yellow solution having the following characteristics data was obtained: acid value 28.6; epoxide value 0.0%. Excess formic acid was distilled off in an oil pump vacuum (0.7 mbar) to a liquid temperature of 120° C. The end product weighed 352.1 g (93.9% yield).

Characteristic data:
Hydroxyl value: OH.V. 104
Saponification value: S.V. 287
Acid value: A.V. 4.7
Iodine value: I.V. 5.8

B. Preparation of a barium-containing copper chromite hydrogenation catalyst 2.6 kg barium nitrate are dissolved in 80 l water and added to 21.8 kg copper nitrate trihydrate solution heated to 70° C. After complete dissolution of the copper nitrate an ammonium chromate (produced by dissolution of 12.6 kg ammonium dichromate in 60 l water and addition of 15 l 28% ammonia solution) is slowly added under agitation. The resulting suspension is agitated after 1 hour, the precipitate filtered off, dried at 110° C. and finally heated at 350°–450° C. The heated product is then digested with 240 l of 10% acetic acid and with 480 l water. The filtered barium copper chromite is dried at 110° C., mixed with 3 wt-% graphite, and then molded and finally processed into 4 mm tablets.

C. Hydrogenation 200 g of the alcohol ester produced above were introduced into a 1-liter autoclave with a magnetic lift stirrer together with 40 g of the barium-containing copper chromite hydrogenation catalyst which was prepared as described above. The alcohol ester was reacted for 6 hours at 220° C. under a hydrogen pressure of 250 bar. The catalyst was filtered off under suction in a heating zone at 100° C. and the filtrate (127 g) distilled.

Three fractions were obtained:

|  | Boiling temp °C. | Pressure mbar | Quantity g | OH.V | S.V. | A.V. |
|---|---|---|---|---|---|---|
| Fraction 1 | 91–155 | 0.01 | 26.1 | 294 | 4.2 | 1.2 |
| Fraction 2 | 155–195 | 0.01 | 66.3 | 513 | 1.4 | 0.3 |
| Distillation residue |  |  | 32.8 | 367 | 0.8 | 7.2 |

Fraction 2 was a colorless crystallizate having a melting equilibrium of 82° C.

EXAMPLE 2

341.9 g (1.0 mol) epoxystearic acid methyl ester (epoxide value 4.68%. M calculated therefrom 341.9) and 66.05 g (1.1 mol) acetic acid and also 2.44 g sodium acetate as catalyst were stirred for 4 hours at 150° C. After the reaction, the A.V. was 28.7 and the epoxide value 0.083%. The catalyst was filtered off and the total quantity (385 g) distilled over in an oil pump vacuum (0.1–0.6 mbar) between 112° and 235° C. 39.2 g (approx. 10%) remained as residue while 322.2 g were obtained as distillate.

The hydrogenation of 320 g of the ester obtained was carried out with 32 g (10%) of the copper chromite hydrogenation catalyst according to Example 1 over a period of 8.5 hours at 220° C./250 bar hydrogen pressure. After the catalyst had been filtered off at 100° C., 220.1 g end product having an OH.V of 465 were obtained. 216.1 g were used for distillation in an oil pump vacuum.

|  | Boiling temp °C. | Pressure mbar | Quantity g | OH.V | S.V. | A.V. |
|---|---|---|---|---|---|---|
| Fraction 1 | 108–180 | 0.05 | 46.6 | 292 |  |  |
| Fraction 2 | 180–205 | 0.06 | 158.0 | 495 | 9.0 | 0.2 |
| Distillation residue |  |  | 7.8 |  |  |  |

Fraction 2 was a colorless crystallizate.

The above description illustrates the surprising and unexpected results of the novel and unobvious combination of process steps of the present invention. This process is widely applicable to a broad range of natural or synthetic starting materials as described herein to produce a wide range of useful end products.

We claim:

1. A process for the production of alkane polyols which comprises reacting epoxidized fatty acids, epoxidized fatty acid esters or mixtures thereof with short-chain alkane carboxylic acid or alkali metal salts thereof under epoxide ring opening conditions to produce an ester alcohol of said epoxidized fatty acid or fatty acid ester, and passing the ester alcohol through a catalytic hydrogenation zone maintained under hydrogenation conditions to convert said ester alcohol to an alkane polyol, and thereafter recovering an alkanepolyol product.

2. The process of claim 1 in which the chain length of the fatty acid moiety of said epoxidized fatty acids or epoxidized fatty acid esters is between about 4 to about 24 carbon atoms and the alcohol moiety of said epoxidized fatty acid esters comprises mono-, di-, or tri-alcohol radicals containing from 1 to about 8 carbon atoms or mixtures thereof.

3. The process of claim 1 in which the epoxidized fatty acids and/or fatty acid esters are derived from oleic acid, soybean oil fatty acid, erucic acid, rapeseed oil fatty acid, linseed oil fatty acid, safflower oil fatty acid, cottonseed oil fatty acid or beef tallow or esters thereof.

4. The process of claim 2 in which the alcohol moiety of said epoxidized fatty acid esters is derived from methanol or glycerol.

5. The process of claim 2 in which said epoxidized fatty acids and/or fatty acid esters comprised mono-epoxidized fatty acids and/or fatty acid esters.

6. The process of claim 2 in which epoxidized technical oleic acid methyl esters are reacted with said short-chain alkane carboxylic acid.

7. The process of claim 2 in which said epoxidized fatty acids or epoxidized fatty acid esters are reacted with a $C_1$ to $C_8$ alkane carboxylic acid.

8. The process of claim 7 in which said epoxidized fatty acids or epoxidized fatty acid esters are reacted with a $C_1$ to $C_3$ alkane carboxylic acid.

9. The process of claim 2 in which the chemical constitution of the alkyl radicals of the alkane carboxylic acids and of the alcohol components of the epoxidized fatty acid esters is the same.

10. The process of claim 1 in which formic acid, acetic acid or propionic acid or alkali metal salts thereof is reacted with said epoxidized fatty acids or epoxidized fatty acid esters.

11. The process of claim 10 in whichj said alkali metal salts comprise sodium or potassium.

12. A process for the production of alkane triols which comprises reacting epoxidized fatty acids or esters thereof where the chain length of the fatty acid moiety is $C_{4-24}$ and the alcohol moiety is $C_1$–$C_3$ with a $C_1$–$C_3$ alkane carboxylic acid or a sodium or potassium salt thereof to produce the corresponding alcohol ester, and then passing said alcohol ester through a catalytic hydrogenation zone containing an hydrogenation catalyst under hydrogenation conditions to produce a corresponding alkane triol, and thereafter recovering said alkane triol product.

13. The process of claim 12 in which the hydrogenation reaction is carried out in the presence of particulate copper- or zinc-containing hydrogenation catalysts at a temperature of from about 150° to about 350° C., pressures of about 200 to about 300 bar with an excess of hydrogen of about 50 to about 500 times the theoretically necessary quantity.

14. The process of claim 13 in which a solvent is present in the hydrogenation reaction.

15. The process of claim 13 in which the hydrogen gas is circulated at a rate of about 1 to about 40 pressure liters per hour and per liter of catalyst volume.

16. The process of claim 12 wherein epoxystearic acid methyl ester is reacted with formic or acetic acid or the sodium or potassium salts thereof.

17. The process of claim 12 wherein technical oleic acid is reacted with formic or acetic acid or the sodium or potassium salts thereof.

18. The process of claim 13 in which the hydrogenation reaction is carried out in the presence of a particulate copper chromite hydrogenation catalyst.

* * * * *